United States Patent

Uchikura et al.

Patent Number: 5,630,416
Date of Patent: May 20, 1997

[54] ULTRASONIC DIAGNOSTIC PROBE

[75] Inventors: Shiro Uchikura; Narutaka Nakao, both of Kawasaki, Japan

[73] Assignee: Fujitsu, Ltd., Kawasaki, Japan

[21] Appl. No.: 503,681

[22] Filed: Jul. 18, 1995

[30] Foreign Application Priority Data

Sep. 19, 1994 [JP] Japan .................. 6-223811

[51] Int. Cl.⁶ .................................................. A61B 8/00
[52] U.S. Cl. .................................................. 128/660.08
[58] Field of Search .................. 128/660.01, 660.08, 128/660.09, 660.1, 662.03, 662.06

[56] References Cited

U.S. PATENT DOCUMENTS

| | | | |
|---|---|---|---|
| 4,375,818 | 3/1983 | Suwaki et al. | 128/662.06 |
| 4,399,703 | 8/1983 | Matzuk | 128/660.1 |
| 4,756,313 | 7/1988 | Terwilliger | 128/662.06 |
| 4,936,307 | 6/1990 | Saito et al. | 128/662.06 |
| 5,070,880 | 12/1991 | Gomez et al. | 128/660.09 |
| 5,255,684 | 10/1993 | Rello | 128/660.1 |
| 5,357,963 | 10/1994 | Mayol et al. | 128/660.1 |
| 5,450,851 | 9/1995 | Hancock | 128/660.1 |

FOREIGN PATENT DOCUMENTS

| | | |
|---|---|---|
| 2-206450 | 8/1990 | Japan . |
| 4-282141 | 10/1992 | Japan . |
| 5-154152 | 6/1993 | Japan . |
| 5-261098 | 10/1993 | Japan . |

*Primary Examiner*—George Manuel
*Attorney, Agent, or Firm*—Staas & Halsey

[57] ABSTRACT

An ultrasonic diagnostic probe includes: a swinging mechanism for swinging a piezoelectric vibrator provided in an accommodating part at an end of a tube-like shaft, around an axis parallel with an ultrasonic transmission and reception face; and a rotating mechanism for rotating the piezoelectric vibrator around an axis perpendicular to the ultrasonic transmission and reception face. The rotating mechanism includes: a pedestal provided with a semicylindrical part; a seat pedestal in which a concave part having a curvature that matches the semicylindrical part is formed so as to rotatably support the pedestal by the semicylindrical part being engaged with the concave part; and a swinging wire for urging the pedestal into a swinging motion.

14 Claims, 10 Drawing Sheets

ULTRASONIC DIAGNOSTIC PROBE

BACKGROUND OF THE INVENTION

1. Field of the Invention

The present invention relates to ultrasonic diagnostic probes and more particularly to a ultrasonic diagnostic probe in which the orientation of a piezoelectric vibrator provided in a shaft is variable.

Recently, ultrasonic diagnosis is extensively used in scanning the body cavity of a human body as well as in scanning the surface of a human body. Ultrasonic scanning in the body cavity provides more detailed information regarding the region diagnosed.

A problem with the scanning of the body cavity is that the pattern of ultrasono-tomographic images is limited because a probe is mounted at the end of a shaft.

2. Description of Prior Art

Nowadays, ultrasono-tomographic diagnosis is extensively practiced by doctors. In the field of ultrasonic diagnosis of the heart, there is known a method called transesophagus echo probe of the heart in which an ultrasonic diagnostic probe is inserted via an mouth and an esophagus for diagnosis of the heart.

A description of a conventional ultrasonic diagnostic probe will be given, with reference to FIGS. 1, 2, 3A, 3B, 3C, 4A, 4B, 4C and 5, using esophagus echo probe of the heart as an example.

FIG. 1 shows the construction of a conventional ultrasonic diagnostic probe 1. The ultrasonic diagnostic probe 1 comprises a tube-like shaft 2 and array piezoelectric vibrators 3a and 3b provided at right angles to each other near the end of the shaft 2. It is known that the transmission and reception of ultrasonic waves by the array piezoelectric vibrators 3a and 3b occur in specific directions. In the construction of FIG. 1 where the two array piezoelectric vibrators are secured in place at right angles to each other, images of only two ultrasono-tomographic sections 4a and 4b can be obtained, the sections 4a and 4b being at right angles to each other.

In order to resolve the above-described disadvantage of the ultrasonic diagnostic probe 1 of FIG. 1 and to enable images of more ultrasono-tomographic sections to be obtained, an ultrasonic diagnostic probe 6 shown in FIG. 2 has been proposed. The ultrasonic diagnostic probe 6 is configured such that an array piezoelectric vibrator 5 is made to rotate. As shown in FIGS. 3A, 3B and 3C, according to the ultrasonic diagnostic probe 6, a section 7 whose image is obtained is made to rotate in response to the rotation of the piezoelectric vibrator 5. Hence, more images can be obtained using the ultrasonic diagnostic probe 6 than using the conventional ultrasonic diagnostic probe 1.

However, the section 7 whose image can be obtained using the construction of the ultrasonic diagnostic probe 6 is always at right angles with respect to the length of the shaft 2, that is, with respect to the direction A indicated by an arrow in FIG. 4A.

Therefore, as shown in FIGS. 4B and 4C, the end of the ultrasonic diagnostic probe 6 should be moved in order to obtain a section that is not perpendicular to the shaft 2. FIG. 4B indicates that a desired section 7 is inclined by an angle $+\theta_1$ to the perpendicular line, and FIG. 4C indicates that a desired section 7 is inclined by an angle $+\theta_1$ to the perpendicular line.

When the piezoelectric vibrator 5 is separated from a wall of an esophagus 8 in which the ultrasonic diagnostic probe 6 is inserted, the propagation characteristic of ultrasonic wave worsens. Therefore, it is necessary to operate the ultrasonic diagnostic probe 6 so that its end is not removed from the inner wall of the esophagus 8. Thus, a problem with the ultrasonic diagnostic probe 6 is that a skill of a doctor is required in order to prevent the end of the piezoelectric vibrator 5 from being removed from the inner wall 8 of the esophagus.

When one needs an image of a section resulting from rotating (clockwise or counterclockwise) the ultrasonic diagnostic probe 6 away from its position shown to the left in FIG. 5 around the central axis of the esophagus 8 by a predetermined angle (for example, $\theta_2$), the shaft 2 should be rotated by an angle $\theta_2$, as shown to the right in FIG. 5 to obtain the required section. The operation of the ultrasonic diagnostic probe 6 is difficult in this respect, too.

SUMMARY OF THE INVENTION

Accordingly, it is an object of the present invention to provide a novel and useful ultrasonic diagnostic probe in which the above-described problems are eliminated.

Another and more specific object of the present invention is to provide an ultrasonic diagnostic probe capable of obtaining images of differently oriented sections with a simple operation.

In order to achieve the objects, the present invention provides an ultrasonic diagnostic probe comprising: a tube-like shaft; a piezoelectric vibrator disposed in an accommodating part provided at an end of the shaft; swinging means which, provided in the accommodating part, swings the piezoelectric vibrator around an axis parallel with an ultrasonic transmission and reception face of the piezoelectric vibrator; and rotating means which, provided in the accommodating part, rotates the piezoelectric vibrator around an axis perpendicular to the ultrasonic transmission and reception face of the piezoelectric vibrator.

Preferably, the swinging means comprises: a pedestal having a vibrator carrying part on which the piezoelectric vibrator is mounted, and a semicylindrical part formed opposite to the vibrator carrying part; a seat pedestal in which a concave part having a curvature that matches the semicylindrical part formed in the pedestal is formed, the seat pedestal swingably supporting the pedestal by the semicylindrical part being engaged with the concave part; and a swinging motion urging member for urging the pedestal into a swinging motion.

The swinging means may comprise:

a pedestal having a vibrator carrying part on which the piezoelectric vibrator is mounted, and a concave part formed opposite to the vibrator carrying part; a seat pedestal in which a semicylindrical part having a curvature that matches the concave part formed in the pedestal is formed, the seat pedestal swingably supporting the pedestal by the concave part being engaged with the semicylindrical part; and a swinging motion urging member for urging the pedestal into a swinging motion.

The swinging means may also comprise:

a pedestal having a vibrator carrying part on which the piezoelectric vibrator is mounted, and a holder part formed opposite to the vibrator carrying part; a seat pedestal in which a bearing part functioning as a bearing for the holder part formed in the pedestal is formed; and a swinging motion urging member for urging the pedestal into a swinging motion.

In an preferred embodiment, the rotating means rotates the piezoelectric vibrator by rotating the seat pedestal.

The present invention offers a preferred construction of the accommodating part in which the accommodating part is formed of a balloon and it is possible to eject a liquid into the accommodating part and to eject the liquid therefrom.

According to the ultrasonic diagnostic probe of the present invention, the piezoelectric vibrator can not only be swung by a swinging mechanism around an axis parallel with the ultrasonic transmission and reception face of the piezoelectric elements, but also rotated by a rotating mechanism around an axis perpendicular to the ultrasonic transmission and reception face. Therefore, by combining the swinging motion and rotating motion of the piezoelectric vibrator, it is possible to orient the ultrasonic transmission and reception face in a variety of directions, while the shaft accommodating the vibrator is allowed to remain stationary.

Accordingly, it is possible to obtain tomographic images of sections oriented in a variety of directions, without moving the shaft or without causing the ultrasonic transmission and reception face of the piezoelectric vibrator to be substantially removed from the target region to be diagnosed. Even when the tomographic section is to be shifted in a direction in which the shaft rotates, it is not necessary to rotated the shaft.

BRIEF DESCRIPTION OF THE DRAWINGS

Other objects and further features of the present invention will be apparent from the following detailed description when read in conjunction with the accompanying drawings, in which.

DESCRIPTION OF THE PREFERRED EMBODIMENTS

Figure 1:
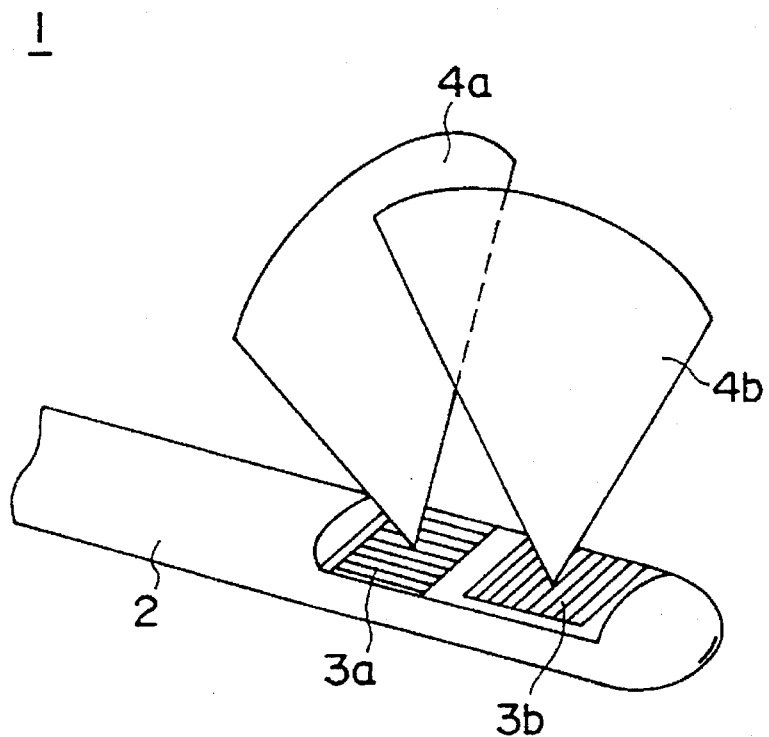
FIG. 1 is a perspective view of a conventional ultrasonic diagnostic probe.
Figure 2:
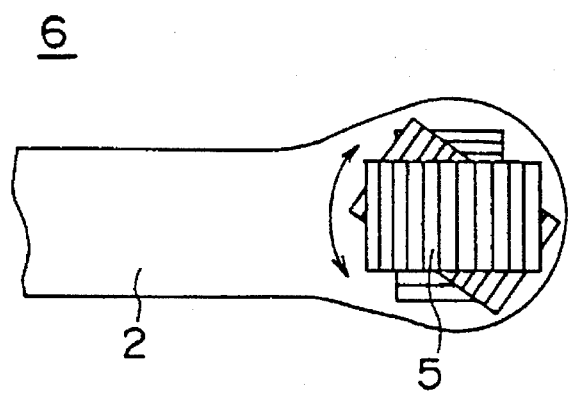
FIG. 2 is a top view of another conventional ultrasonic diagnostic probe.
Figure 3A:
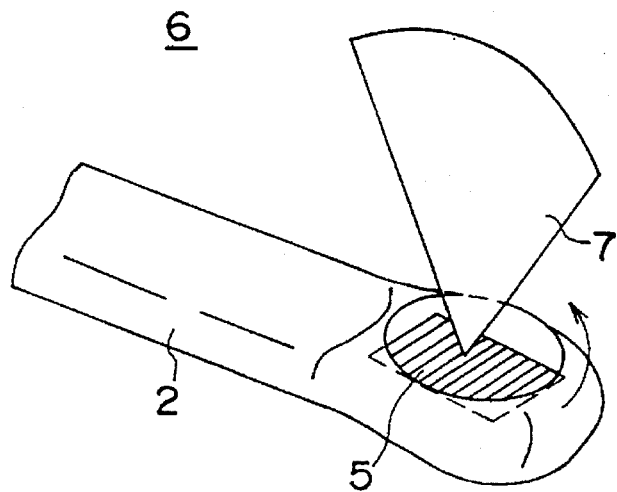
FIGS. 3A through 3C explain the operation of the piezoelectric vibrator of the conventional ultrasonic diagnostic probe shown in FIG. 2.
Figure 3B:
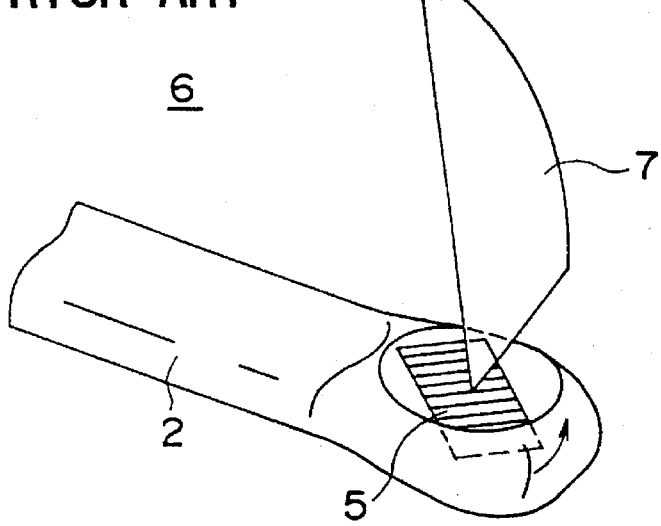
Figure 3C:
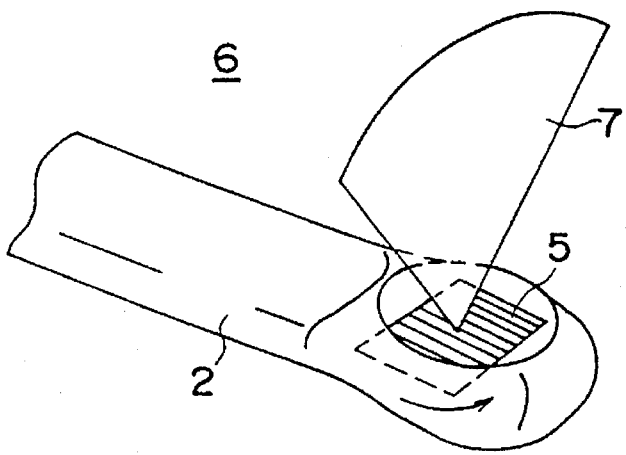
Figure 4A:
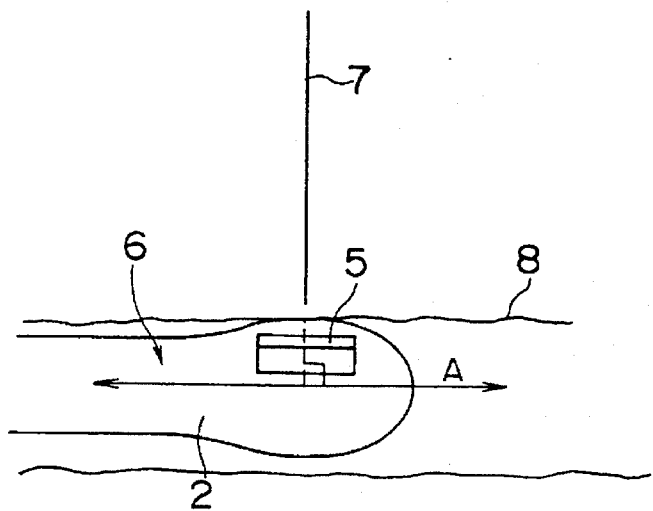
FIGS. 4A through 4C explain a problem with the conventional ultrasonic probe shown in FIG. 2.
Figure 4B:
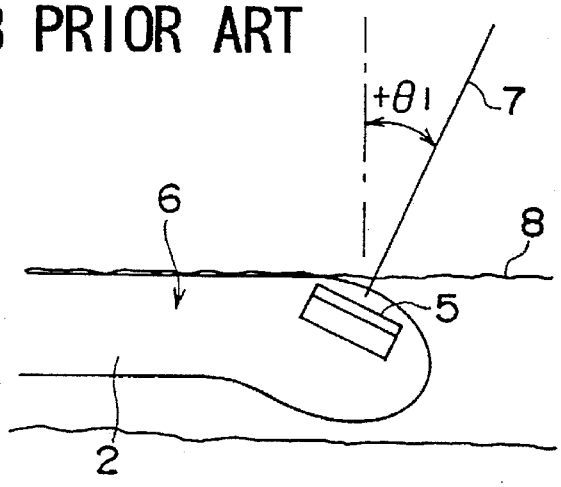
Figure 4C:
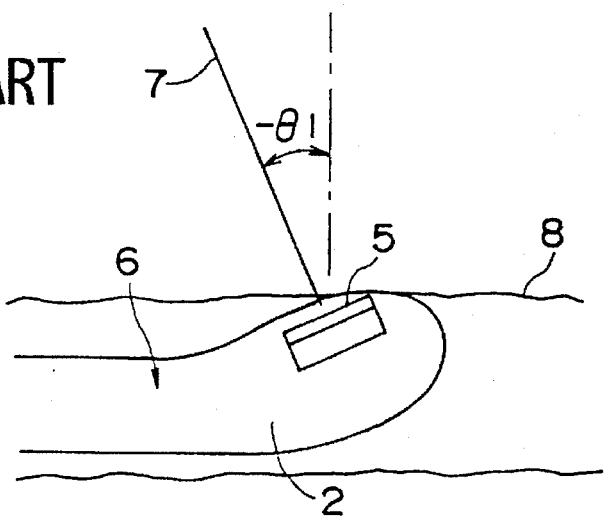
Figure 5:
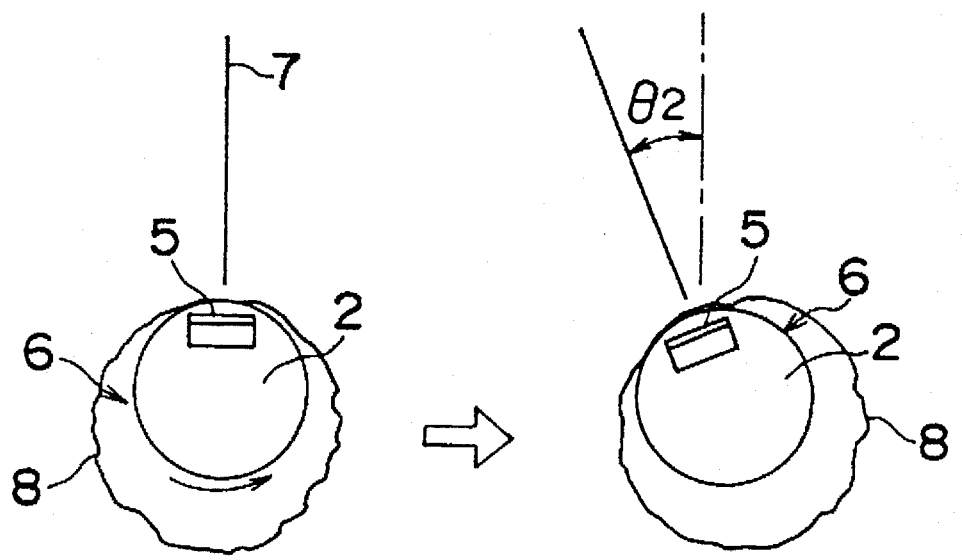
FIG. 5 explains another problem with the conventional ultrasonic diagnostic probe shown in FIG. 2.
Figure 6A:
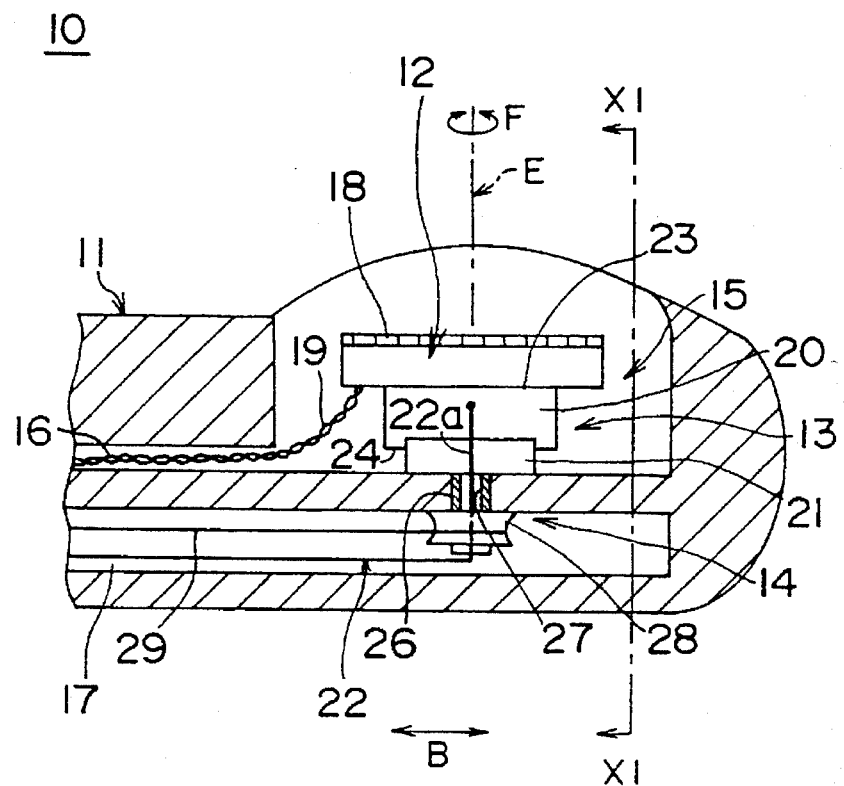
FIG. 6A is a longitudinal sectional view of an ultrasonic diagnostic probe according to a first embodiment of the present invention.
Figure 6B:
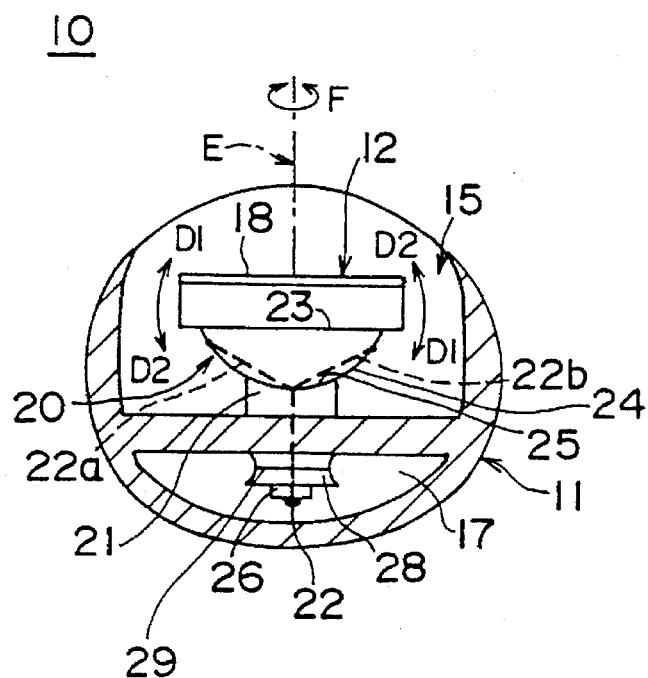
FIG. 6B is a front sectional view of the ultrasonic diagnostic probe according to the first embodiment.

FIGS. 6A and 6B show an ultrasonic diagnostic probe 10 according to a first embodiment of the present invention. FIG. 6A is a longitudinal sectional view of the ultrasonic diagnostic probe 10, and FIG. 6B is a sectional view taken along the line X1—X1 of FIG. 6A. In the description of the embodiments given below, it is assumed that the present invention is applied to the transesophagus ultrasonic echo probe of the heart. Since the feature of the present invention concerns the end part of the ultrasonic diagnostic probe, the diagrams referred to in the description below generally show only the end part of the ultrasonic diagnostic probe.

The ultrasonic diagnostic probe 10 according to the first embodiment generally comprises a tube-like shaft 11, a piezoelectric vibrator 12, a swinging mechanism 13 and a rotating mechanism 14.

For example, the shaft 11 is a tube made of a resin and has at its end an accommodating part 15 which communicates with a first passage 16. A second passage 17 extending to the end of the shaft so as to be directly below the accommodating part 15 is provided in the interior of the shaft 11. The passages 16 and 17 also extend to the other end of the shaft 11 opposite to end where the accommodating part 15 is formed.

The piezoelectric vibrator 12 is accommodated in the accommodating part 15 formed in the shaft 11. The piezoelectric vibrator 12 is an array piezoelectric vibrator and has an ultrasonic transmission and reception face 18 formed on its surface. The ultrasonic transmission and reception face 18 is configured such that piezoelectric elements $18_1$, $18_2$ . . . (see FIGS. 8B and 8C) formed of a piezoelectric body like a piezoelectric ceramic and having the shape of a rectangular slip are arranged in the longitudinal direction (indicated by an arrow B in FIG. 6A). Accordingly, the ultrasonic transmission and reception face 18 has a rectangular shape. A backing member (not shown) is provided at the back of the ultrasonic transmission and reception face 18. Signal transmission and reception cables 19 for the piezoelectric elements $18_1$, $18_2$ . . . extend from the side of the ultrasonic transmission and reception face 18. The cables 19 extend to the opposite end of the shaft 11 through the first passage 16.

The swinging mechanism 13 is provided in the accommodating part 15 and has the function of swinging the piezoelectric vibrator 12 around an axis (indicated by a chain line C in FIGS. 8A, 8B and 8C) parallel with the ultrasonic transmission and reception face 18. The swinging mechanism 13 generally comprises a pedestal 20, a seat pedestal 21 and a flexible wire 22 (hereinafter, referred to as a singing wire) which acts as a swinging motion urging member.

The pedestal 20 is formed of, for example, a hard resin. The pedestal 20 is constructed of a vibrator carrying part 23 on which the piezoelectric vibrator 12 is mounted, and a semicylindrical part 24 (see FIGS. 6B, 7B, 8A, 8B and 8C) formed opposite to the vibrator carrying part 23, the vibrator carrying part 23 and the semicylindrical part 24 being integral with each other.

Figure 7B:
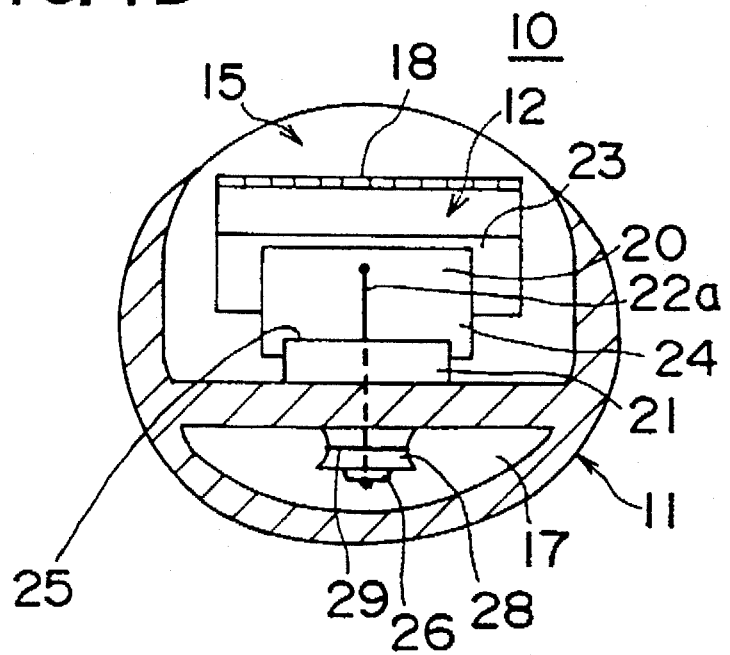
FIG. 7B is a front sectional view of the ultrasonic diagnostic probe according to the first embodiment, wherein the piezoelectric vibrator is swung and rotated with respect to its position shown in FIG. 6B by the swinging mechanism.
Figure 8A:
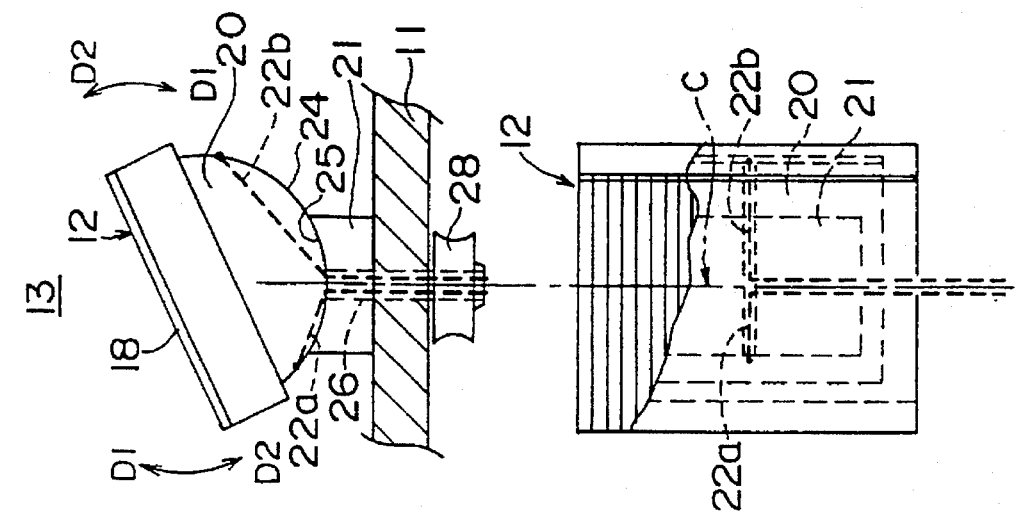
FIGS. 8A through 8C explain the operation of the swinging mechanism.
Figure 8B:
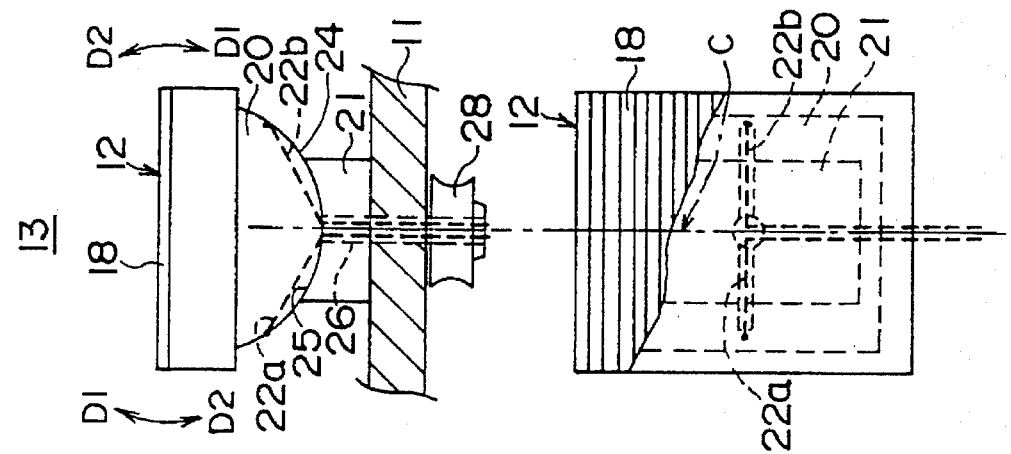
Figure 8C:
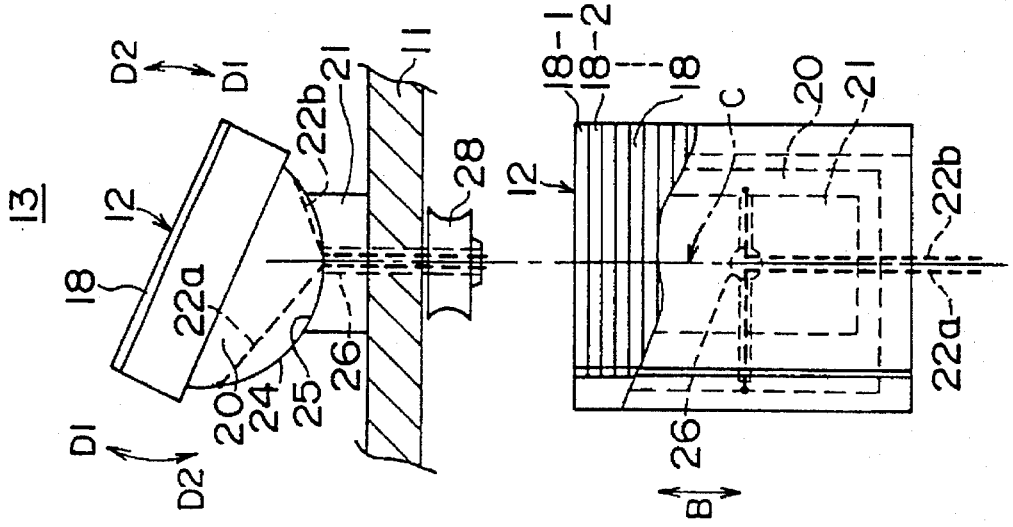

The seat pedestal 21 is also formed of a hard resin and has a concave part 25 (see FIGS. 6B, 7B, 8A, 8B and 8C) having a curvature that matches the semicylindrical part 24 formed in the pedestal 20. The semicylindrical part 24 is engaged with the concave part 25 formed in the seat pedestal 21 in such a manner that the semicylindrical part 24 is allowed to move in the concave part 25 but cannot be detached therefrom. In other words, the seat pedestal 21 swingably supports the pedestal 20 in a state in which the semicylindrical part 24 is engaged with the concave part 25. Referring to FIGS. 8A, 8B and 8C, the direction of the swinging motion of the pedestal 20 with respect to the seat pedestal 21 is indicated by D1 and D2.

The swinging wire 22 is a set of two component wires 22a and 22b. For example, a resin wire having a small elasticity is used to form the swinging wire 22. For this reason, the swinging wire 22 is flexible and can be bent in an arbitrary manner. The swinging wire 22 is provided in the second passage 17 formed in the shaft 11. The end of the swinging wire 22 is led through a hollow part 27 of a rotation shaft 26 of the rotating mechanism 14 described later to reach the accommodating part 15.

The component wire 22a constituting the swinging wire 22 is connected to an upper portion of the semicylindrical part 24. The other component wire 22b also constituting the swinging wire 22 is connected to another upper portion of the semicylindrical part 24. As a result, a fork is formed in the accommodating part 15. At the other end of the shaft 11 opposite to the end in which the accommodating part 15 is provided, the swinging wire 22 is led out of the shaft 11.

A description will now be given of the operation of the swinging mechanism 13 having the above-described construction, with reference to FIGS. 6A, 6B, 8A, 8B and 8C. FIGS. 8A through 8C explain the operation of the swinging mechanism. Specifically, the diagrams at the top of FIGS. 8A, 8B and 8C are longitudinal views of the swinging mechanism, and the diagrams at the bottom of FIGS. 8A, 8B and 8C are partially sectioned top views of the swinging mechanism.

The pedestal 20 is supported by the seat pedestal 21 so as to be swingable in the D1 and D2 directions as indicated in FIGS. 8A through 8C. As described above, the component wires 22a and 22b are connected to the respective upper portions of the semicylindrical part 24 formed in the pedestal 20. Therefore, by pulling the component wire 22b constituting the swinging wire 22, the pedestal 20 is swung on the seat pedestal 21 in the D1 direction, as shown in FIG. 8A.

By pulling the component wire 22a constituting the swinging wire 22, the pedestal 20 is swung on the seat pedestal 21 in the D2 direction, as shown in FIG. 8C. By setting a tensile force applied to the component wires 22a and 22b at a same level, the pedestal 20 remains horizontal on the seat pedestal 21, as shown in FIG. 8B.

As has been described above, the pedestal 20 can be made to swing by adjusting a tensile force applied to the component wires 22a and 22b constituting the swinging wire 22 and to remain stationary at a desired angle. As has been described before, the piezoelectric vibrator 12 is provided in the vibrator carrying part 23 formed in the pedestal 20. Therefore, by operating the component wires 22a and 22b so as to swing the pedestal 20, it is possible to swing the piezoelectric vibrator 12 and to hold it at a desired position.

Figure 7A:
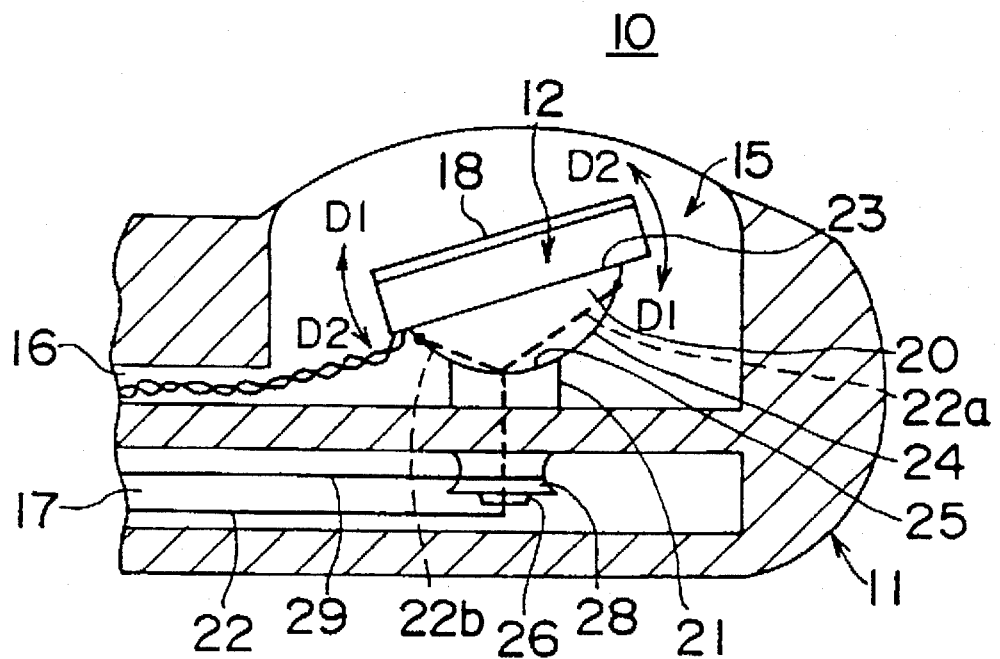
FIG. 7A is a longitudinal sectional view of the ultrasonic diagnostic probe according to the first embodiment, wherein the piezoelectric vibrator is swung and rotated with respect to its position shown in FIG. 6A by a swinging mechanism.

A description will now be given of the rotating mechanism 14, with reference to FIGS. 6A, 6B, 7A and 7B. FIG. 7A is a longitudinal sectional view of the ultrasonic diagnostic probe according to the first embodiment, wherein the piezoelectric vibrator is swung with respect to its position shown in FIG. 6A by a swinging mechanism. FIG. 7B is a front sectional view of the ultrasonic diagnostic probe according to the first embodiment, wherein the piezoelectric vibrator is swung and rotated with respect to its position shown in FIG. 6B by the swinging mechanism (the rotating motion will be described later).The rotating mechanism 14 has the function of rotating the piezoelectric vibrator 12 around an axis (indicated by E in FIGS. 6A and 6B) perpendicular to the ultrasonic transmission and reception face 18 (the direction of rotation is indicated by F in FIGS. 6A and 6B). The rotating mechanism 14 of the first embodiment generally comprises a rotation shaft 26, a pulley 28, a flexible wire 29 (hereinafter, referred to as a rotating wire) and the seat pedestal 21 which also constitutes the swinging mechanism 13.

The rotation shaft 26 is rotatably inserted in a communicating hole which connects the accommodating part 15 formed in the shaft 11 to the second passage 17. As described previously, the hollow part 27 is formed inside the rotation shaft 26. The upper end of the rotation shaft 26 projects into the accommodating part 15, the seat pedestal 21 being fixed to the projecting part (the upper end) of the rotation shaft 26. The lower end of the rotation shaft 26 projects into the second passage 17, the pulley 28 being fixed to the projecting part (the lower end) of the rotation shaft 26. Since the seat pedestal 21 is fixed to the rotation shaft 26, the seat pedestal 21 is rotated as the pulley 28 is rotated.

The rotating wire 28 is wound around the pulley 28. As in the case of the swinging wire 22, a resin wire having a small elasticity is used as the rotating wire 29. At the other end of the shaft 11 opposite to the end in which the accommodating part 15 is provided, the rotating wire 29 is led out of the shaft 11.

Therefore, by operating the rotating wire 29, the seat pedestal 21 as well as the pulley 29 is rotated. Since the pedestal 20 provided with the piezoelectric vibrator 12 is supported by the seat pedestal 21, the piezoelectric vibrator 12 can be rotated by operating the rotating wire 29. FIGS. 7A and 7B show a state in which the seat pedestal 21 is rotated by 90° with respect to the state shown in FIGS. 6A and 6B, by operating the rotating wire 29.

In this way, the first embodiment makes it possible to rotate the piezoelectric vibrator 12 by operating the rotating wire 29 to rotate the seat pedestal 21. It is also possible to maintain the piezoelectric vibrator 12 at a desired position obtained as a result of the rotation. The operation of the swinging mechanism 13 and the operation of the rotating mechanism are independent of each other. Hence, as shown in FIGS. 7A and 7B, it is possible to swing the pedestal 20 in the D1 or D2 direction (FIGS. 7A and 7B show the pedestal 20 swung in the D2 direction) while at the same time rotating the seat pedestal 21.

To summarize, the ultrasonic diagnostic probe 10 of the first embodiment enables the piezoelectric vibrator 12 to swing around the axis indicated by the chain line C, parallel with the ultrasonic transmission and reception face 18, using the swinging mechanism 13. The piezoelectric vibrator 12 is also rotatable around the axis indicated by E, perpendicular to the ultrasonic transmission and reception face 18, using the rotating mechanism 14. Accordingly, by combining the swinging motion and the rotating motion, the ultrasonic transmission and reception face 18 of the piezoelectric vibrator 12 can have a variety of orientations without moving the shaft 11, as shown in FIGS. 9A and 9B, which are perspective views showing the swinging motion and rotating motion of the ultrasonic diagnostic probe according to the first embodiment.

Figure 9A:
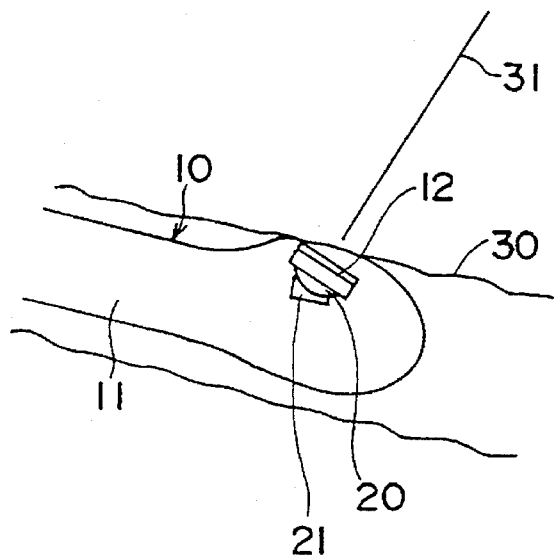
FIGS. 9A through 9C explain the swinging motion and the rotating motion of the piezoelectric vibrator of the ultrasonic diagnostic probe according to the first embodiment.
Figure 9B:
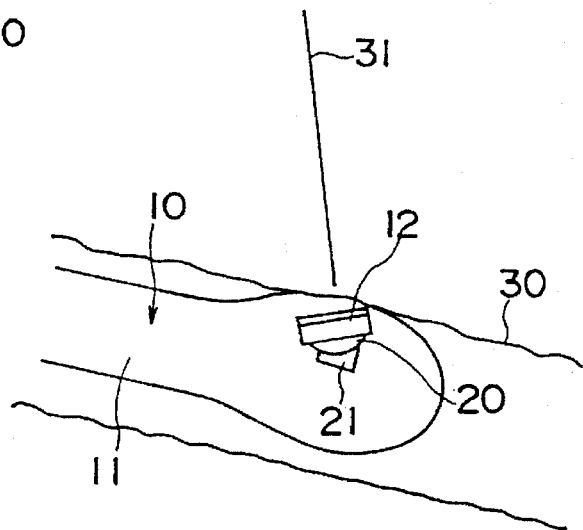
Figure 9C:
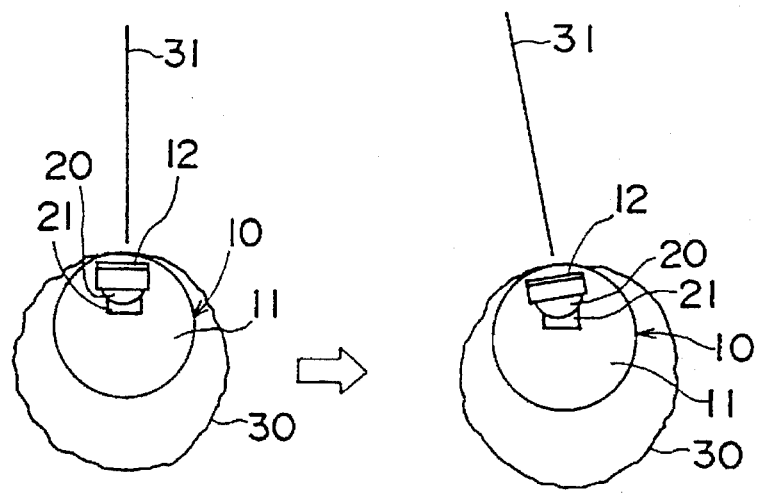

The present invention ensures that a tomographic section 31 can be oriented at a variety of angles without moving the shaft 11 and without the ultrasonic transmission and reception face 18 of the piezoelectric vibrator 12 being substantially removed from a portion diagnosed (in the example shown in FIGS. 9A, 9B and 9C, it is assumed that a blood vessel 30 is diagnosed). Further, as shown in FIG. 9C, which is a lateral sectional view showing the ultrasonic diagnostic probe according to the first embodiment inserted in the blood vessel, even when the tomographic section is to be shifted in a direction in which the shaft 11 rotates, it is not necessary to rotate the shaft 11. The desired orientation of the tomographic section can be achieved by swinging or rotating the piezoelectric vibrator 12.

Since the ultrasonic diagnostic probe 10 according to the first embodiment enables the tomographic section to be oriented at a variety of angles without rotating the shaft 11, ultrasono-tomography can be easily performed without requiring much skill on the part of a doctor.

Further, the ultrasonic diagnostic probe 10 of the first embodiment is configured such that the first passage 16 is connected to a liquid supply unit (not shown) capable of injecting a liquid to the first passage 16 communicating with the accommodating part 15 or ejecting a liquid therefrom. Also, at least the accommodating part 15 is formed of an inflatable balloon so that the accommodating part 15 inflate when a liquid is injected from the liquid supply unit and deflate when the liquid is ejected. Hence, it is possible to perform an operation of enlarging the diameter of the blood vessel 30 affected by an infarction, by inflating the accommodating part 15.

A description will now be given of a second embodiment of the present invention.

Figure 10A:
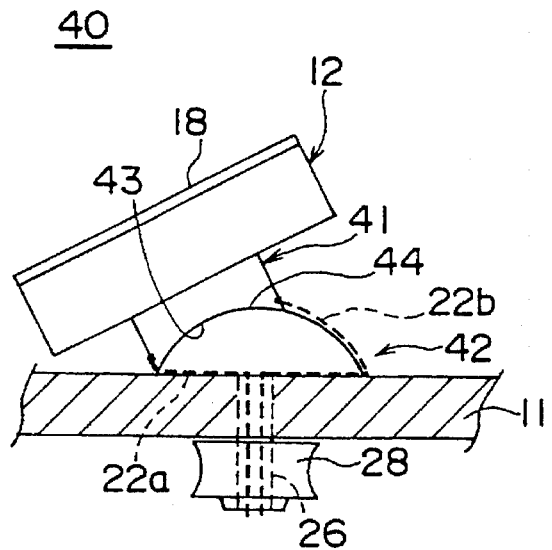
FIG. 10A is a side view of an ultrasonic diagnostic probe according to a second embodiment of the present invention.
Figure 10B:
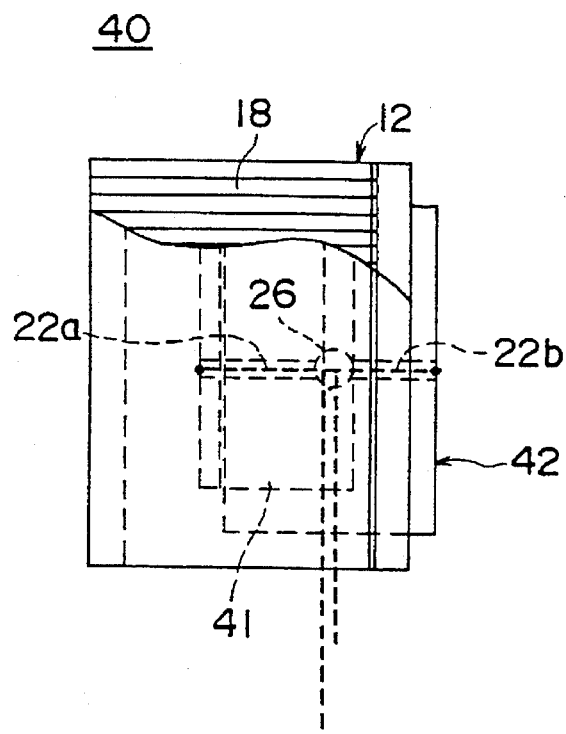
FIG. 10B is a partially sectioned top view of the ultrasonic diagnostic probe according to the second embodiment.

FIGS. 10A and 10B show an ultrasonic diagnostic probe 40 according to a second embodiment. FIG. 10A is a side view of the ultrasonic diagnostic probe 40, and FIG. 10B is a partially sectioned top view thereof. Those components of the ultrasonic diagnostic probe 40 that are the same as the components of the ultrasonic diagnostic probe 10 according to the first embodiment are designated by the same reference numerals and the description thereof is omitted.

The ultrasonic diagnostic probe 40 is configured such that a concave surface 43 is formed in a pedestal 41 on which the piezoelectric vibrator 12 is provided, and a semicylindrical part 44 that matches the concave surface 43 is formed in a seat pedestal 42 for supporting the pedestal 41. In accordance with this construction, the two component wires 22a and 22b constituting the swinging wire 22 are connected to the concave surface 43 of the pedestal 41.

Like the ultrasonic diagnostic probe 10 according to the first embodiment, the ultrasonic diagnostic probe 40 having the concave surface 43 and the semicylindrical part 44 enables the piezoelectric vibrator 12 to swing and rotate. Hence, like the ultrasonic diagnostic probe 10 according to the first embodiment, it is possible to obtain an ultrasonotomographic image of the desired section 31 without the ultrasonic transmission and reception surface 18 being removed substantially from the portion diagnosed.

A description will now be given of a third embodiment of the present invention.

Figure 11A:
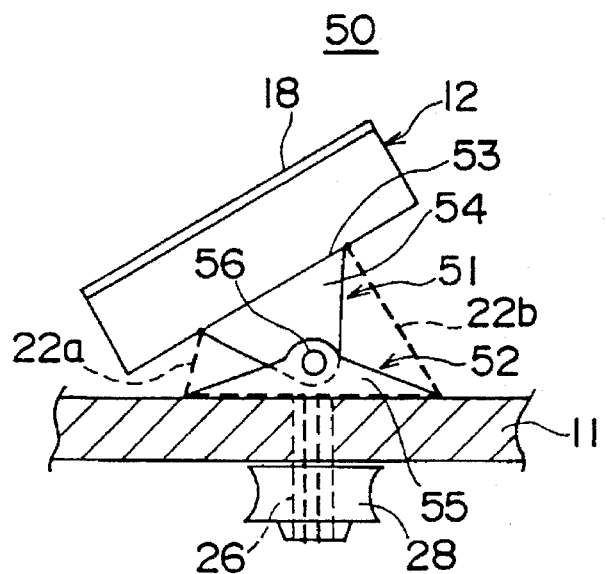
FIG. 11A is a side view of an ultrasonic diagnostic probe according to a third embodiment of the present invention.
Figure 11B:
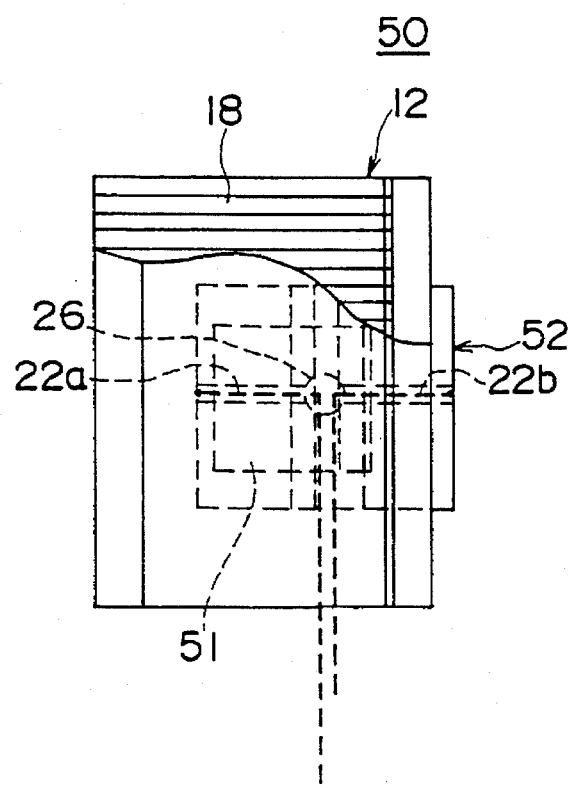
FIG. 11B is a partially sectioned top view of the ultrasonic diagnostic probe according to the third embodiment.

FIGS. 11A and 11B show an ultrasonic diagnostic probe 50 according to a third embodiment of the present invention. FIG. 11A is a side view of the ultrasonic diagnostic probe 50, and FIG. 11B is a partially sectioned top view thereof. Those components of the ultrasonic diagnostic probe 50 that are the same as the components of the ultrasonic diagnostic probe 10 according to the first embodiment are designated by the same reference numerals and the description thereof is omitted.

In the ultrasonic diagnostic probe 50, a holder part 54 is provided in the pedestal 51 to be opposite to a vibrator carrying part 53. Further, a bearing part 55 that functions as a bearing for the holder part 54 is formed in a seat pedestal 52.

The holder part 54 formed in the pedestal 51 and the bearing part 55 formed in the seat pedestal 52 are coupled by a pin 56 so that the pedestal 51 is rotatable. In other words, by the bearing part 55 serving as the bearing for the holder part 54, the pedestal 51 is swingably supported by the seat pedestal 52. The component wires 22a and 22b constituting the swinging wire 22 are connected to respective upper portions of the holder part 54 formed in the pedestal 51.

In the ultrasonic diagnostic probe 50, it is possible to swing and rotate the piezoelectric vibrator 12 using the construction in which the pedestal 51 is swingably fitted to the seat pedestal 52, the holder part 54 is provided in the pedestal 51, and the bearing part 55 for the holder part 54 is provided in the seat pedestal 52. Therefore, like the ultrasonic diagnostic probe 10 and 40 of the first and second embodiments, respectively, it is possible to obtain an image of the desired section 31 without the ultrasonic transmission and reception part 18 being substantially removed from the portion diagnosed.

While the embodiments described above use the construction in which the wires 22 and 29 are used as a swinging motion urging member and a rotating motion urging member, respectively, the swinging motion urging member and the rotating motion urging member are not limited to wires. For example, springs or gears may be used alternatively.

The present invention is not limited to the above described embodiments, and variations and modifications may be made without departing from the scope of the present invention.

What is claimed is:

1. An ultrasonic diagnostic probe comprising:

a tube-like shaft having an end and an accommodating part provided at the end;

a piezoelectric vibrator disposed in said accommodating part, having an ultrasonic transmission and reception face;

swinging means provided in said accommodating part, which swings said piezoelectric vibrator around an axis parallel with the ultrasonic transmission and reception face of said piezoelectric vibrator, the swinging means having a relative position which is substantially fixed with respect to the tube-like shaft; and rotating means provided in said accommodating part, which rotates said piezoelectric vibrator around an axis perpendicular to the ultrasonic transmission and reception face of said piezoelectric vibrator.

2. The ultrasonic diagnostic probe as claimed in claim 1, wherein said swinging means comprises:

a pedestal having a vibrator carrying part on which said piezoelectric vibrator is mounted, and a semicylindrical part formed opposite to said vibrator carrying part;

a seat pedestal in which a concave part having a curvature that matches the semicylindrical part formed in said pedestal is formed, said seat pedestal swingably supporting said pedestal by said semicylindrical part being engaged with said concave part and movable with respect to said concave part; and a swinging motion urging member for urging said pedestal into a swinging motion.

3. The ultrasonic diagnostic probe as claimed in claim 2, wherein said rotating means rotates said piezoelectric vibrator by rotating said seat pedestal.

4. The ultrasonic diagnostic probe as claimed in claim 3, wherein said accommodating part is formed of an inflatable balloon and allows a liquid to be injected therein and ejected therefrom.

5. The ultrasonic diagnostic probe as claimed in claim 2, wherein said accommodating part is formed of an inflatable balloon and allows a liquid to be injected therein and ejected therefrom.

6. The ultrasonic diagnostic probe as claimed in claim 1, wherein said swinging means comprises:

a pedestal having a vibrator carrying a part on which said piezoelectric vibrator is mounted, and a concave part formed opposite to said vibrator carrying part;

a seat pedestal in which a semicylindrical part having a curvature that matches the concave part formed in said pedestal is formed, said seat pedestal swingably supporting said pedestal by said concave part being engaged with said semicylindrical part and movable with respect to said semicylindrical part; and a swinging motion urging member for urging said pedestal into a swinging motion.

7. The ultrasonic diagnostic probe as claimed in claim 6, wherein said rotating means rotates said piezoelectric vibrator by rotating said seat pedestal.

8. The ultrasonic diagnostic probe as claimed in claim 7, wherein said accommodating part is formed of an inflatable balloon and allows a liquid to be injected therein and ejected therefrom.

9. The ultrasonic diagnostic probe as claimed in claim 6, wherein said accommodating part is formed of an inflatable balloon and allows a liquid to be injected therein and ejected therefrom.

10. The ultrasonic diagnostic probe as claimed in claim 1, wherein said swinging means comprises:

a pedestal having a vibrator carrying part on which said piezoelectric vibrator is mounted, and a holder part formed opposite to said vibrator carrying part;

a seat pedestal in which a bearing part functioning as a bearing for rotatably supporting the holder part formed in said pedestal is formed; and a swinging motion urging member for urging said pedestal into a swinging motion.

11. The ultrasonic diagnostic probe as claimed in claim 10, wherein said rotating means rotates said piezoelectric vibrator by rotating said seat pedestal.

12. The ultrasonic diagnostic probe as claimed in claim 11, wherein said accommodating part is formed of an inflatable balloon and allows a liquid to be injected therein and ejected therefrom.

13. The ultrasonic diagnostic probe as claimed in claim 10, wherein said accommodating part is formed of an inflatable balloon and allows a liquid to be injected therein and ejected therefrom.

14. The ultrasonic diagnostic probe as claimed in claim 1, wherein said accommodating part is formed of an inflatable balloon and allows a liquid to be injected therein and ejected therefrom.

* * * * *